(12) United States Patent
Grinstein et al.

(10) Patent No.: US 6,816,790 B2
(45) Date of Patent: Nov. 9, 2004

(54) METHOD AND APPARATUS FOR DETERMINING GENE EXPRESSION LEVELS

(75) Inventors: Geoffrey Grinstein, New York, NY (US); Glenn Allen Held, Pelham, NY (US); Yuhai Tu, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 10/365,891

(22) Filed: Feb. 13, 2003

(65) Prior Publication Data

US 2004/0128082 A1 Jul. 1, 2004

Related U.S. Application Data

(60) Provisional application No. 60/437,232, filed on Dec. 31, 2002.

(51) Int. Cl.[7] ........................... G06F 19/00; G01N 31/00
(52) U.S. Cl. ............................. 702/23; 702/19; 702/20; 702/27; 435/6
(58) Field of Search ............................. 702/19, 20, 22, 702/23, 27; 435/6, 7.92, 69.1, 91.2, 973

(56) References Cited

U.S. PATENT DOCUMENTS

| | | | | |
|---|---|---|---|---|
| 6,228,593 B1 | | 5/2001 | Lipshutz et al. ............... | 435/6 |
| 6,251,601 B1 | * | 6/2001 | Bao et al. ....................... | 435/6 |
| 6,510,391 B2 | * | 1/2003 | Balaban ........................ | 702/19 |
| 6,516,276 B1 | * | 2/2003 | Ghandour et al. ............. | 702/27 |
| 6,546,340 B2 | * | 4/2003 | Lipshutz et al. ............... | 702/20 |
| 2003/0186234 A1 | * | 10/2003 | Kurn .............................. | 435/6 |

OTHER PUBLICATIONS

Balaban, David, "Computer Software Products for Nucleic Acid Hybridization Analysis," U.S. patent application No. 2002–0102547–A1 (Aug. 1, 2002).

DeRisi et al., "Exploring the Metabolic and Genetic Control of Gene Expression on a Genomic Scale," Science, vol. 278, pp. 680–686 (Oct. 1997).

(List continued on next page.)

*Primary Examiner*—John Barlow
*Assistant Examiner*—John Le
(74) *Attorney, Agent, or Firm*—Ryan, Mason & Lewis, LLP; Casey P. August, Esq.

(57) ABSTRACT

Techniques for analyzing gene expression levels are provided. In one aspect of the invention, the technique provides a method for determining a concentration level of a target nucleic acid, the target nucleic acid comprising at least one target oligonucleotide. The method determines (i) a measure of affinity value of the target oligonucleotide with a probe oligonucleotide; and (ii) a hybridization intensity value for the target oligonucleotide and the probe oligonucleotide at a probe spot. The measure of affinity value and the hybridization intensity value are used to determine the concentration level of the target nucleic acid.

17 Claims, 4 Drawing Sheets

OTHER PUBLICATIONS

Li et al., "Model–Based Analysis of Oligonucleotide Arrays: Expression Index Computation and Outlier Detection," PNAS, vol. 98, No. 1, pp. 31–36 (Jan. 2001).

Lipshutz et al., "Computer–Aided Probability Base Calling for Arrays of Nucleic Acid Probes on Chips," U.S. patent application No. 2002–0058261–A1 (May 16, 2002).

Lipshutz et al., "High Density Synthetic Oligonucleotide Arrays," Nature Genetics Supplement, vol. 21, pp. 20–24 (Jan. 1999).

Liu et al., "System and Computer Software Products for Comparative Gene Expression Analysis," U.S. patent application No. 2002–0103604–A1 (Aug. 1, 2002).

Lockhart et al., "Expression Monitoring by Hybridization to High–Density Oligonucleotide Arrays," Nature Biotechnology, vol. 14, pp. 1675–1680 (Dec. 1996).

SantaLucia, Jr., John, "A Unified View of Polymer, Dumbbell, and Oligonucleotide DNA Nearest–Neighbor Thermodynamics," Proc. Nat'l Acad. Sci. USA, vol. 95, pp. 1460–1465 (Feb. 1998).

Selinger et al., "RNA Expression Analysis Using a 30 Base Pair Resolution *Escherichia coli* Genome Array," Nature Biotechnology, vol. 18, pp. 1262–1268 (Dec. 2000).

* cited by examiner

METHOD AND APPARATUS FOR DETERMINING GENE EXPRESSION LEVELS

CROSS REFERENCE TO RELATED APPLICATIONS

This application claims the benefit of U.S. Provisional Application No. 60/437,232, filed Dec. 31, 2002.

FIELD OF THE INVENTION

The present invention relates to gene expression levels and, more particularly, to the determination of gene expression levels using nucleic acid microarrays.

BACKGROUND OF THE INVENTION

The study of gene expression levels is a focus of current research. Gene expression analysis may be carried out using microarrays. Microarrays allow for the rapid analysis of large quantities of genetic material. For a detailed discussion of microarrays, see P. O. Brown, et al., "Exploring the New World of the Genome With DNA Microarrays," Nature Genetics v. 21, p. 33 (1999); R. J. Lipshutz, et al., "High Density Synthetic Oligonucleotide Arrays," Nature Genetics v. 21, p. 20 (1999), the disclosures of which are incorporated by reference herein. Microarrays allow researchers to analyze the genetic information in cells, e.g., genes, to determine whether each gene is being expressed in the cell, and if so, to quantify the expression level. Since gene expression levels play a central role in determining the phenotype, the observable characteristics of the cell, the gene expression levels play a crucial part in diagnosing disease states of the cell (for example, identifying cells that are, or likely to become, cancerous), in understanding cell cycles and differentiation and in casting light upon the complex spectrum of behaviors and changes in a cell.

Microarray technologies take several different forms. Some microarrays contain billions of relatively short oligonucleotides, i.e., less than 100 base pairs, of single DeoxyriboNucleic Acid (DNA) strands, termed "probe oligonucleotides," bonded to a substrate. Each of the probe oligonucleotides represents an "unzipped" piece of a gene available for binding with a complementary strand to which the probe oligonucleotide can be "zipped." Ideally, many identical copies of each probe oligonucleotide are deposited onto an area, i.e., about 20 microns square, termed a "probe spot," on the substrate. A collection of probe spots on a microarray can represent thousands of genes.

Oligonucleotide sequences which are representative of the genes of interest within a cell are called target oligonucleotides. The concentration of target oligonucleotides is a measure of gene expression levels. A number of target oligonucleotides may be complementary to the probe oligonucleotides. Each target oligonucleotide has a strong affinity for bonding, i.e., hybridizing, with the probe oligonucleotide to which it is complementary. Thus, once a solution containing target oligonucleotides is introduced into the microarray, those probe oligonucleotides of the microarray that are complementary, or nearly complementary, to target oligonucleotides in the solution will hybridize with those target oligonucleotides, producing probe spots of the microarray containing hybridized probe oligonucleotide and target oligonucleotide double strands. Other spots wherein the probe oligonucleotides are not complementary to any target oligonucleotides in the solution will contain only the unhybridized, single-stranded probe oligonucleotides. Fluorescent tags on the target oligonucleotides allow for the detection of probe spots containing hybridized probe oligonucleotides and target oligonucleotides. Thus, the target oligonucleotides present in the solution may be determined. Moreover, the intensity of the fluorescence provides a measure of how much of each target oligonucleotide is present in the target solution, and hence in the original cell.

Gene expression analysis using conventional methods, such as the Affymetrix® Genechips® and algorithms has several shortcomings. For example, in the Affymetrix® technology, each gene is typically represented by a plurality of different probes of short length, i.e., about 25 nucleotide base pairs. Since all the target oligonucleotides representing a given gene are present in roughly equal concentrations, measured intensity values of all the probe spots corresponding to that gene are expected to be virtually identical. In fact, however, there are typically sizable variations in measured hybridization intensity values among the probe spots representing a particular gene. These variations may be due to, for example, cross-hybridization, secondary structure (hybridization of segments of a single target oligonucleotide or probe oligonucleotide with one other), or stronger tendency for certain complementary pairs to hybridize than for others. Variations greatly complicate the task of determining a unique and correct expression level for each gene in the target solution.

Thus, there exists a need for an accurate and efficient technique for determining gene expression levels.

SUMMARY OF THE INVENTION

The present invention provides techniques for analyzing gene expression. In one aspect of the invention, the technique provides a method for determining a concentration level of a target nucleic acid, the target nucleic acid comprising at least one target oligonucleotide. The method determines (i) a measure of affinity value of the target oligonucleotide with a probe oligonucleotide; and (ii) a hybridization intensity value for the target oligonucleotide and the probe oligonucleotide at a probe spot. The measure of affinity value and the hybridization intensity value are used to determine the concentration level of the target nucleic acid.

The measure of affinity value may comprise a free energy of hybridization of the target oligonucleotide with the probe oligonucleotide. Further, the measure of affinity value may comprise a net rate of hybridization of the target oligonucleotide with the probe oligonucleotide.

A more complete understanding of the present invention, as well as further features and advantages of the present invention, will be obtained by reference to the following detailed description and drawings.

DETAILED DESCRIPTION OF PREFERRED EMBODIMENTS

The present invention will be described below in the context of an illustrative gene expression analysis using the concentration level of a target nucleic acid. However, it is to be understood that the teachings of the present invention are generally applicable to gene expression analysis and should not be construed as being limited to any particular methodology for gene expression level analysis.

The following definitions are provided:

Target nucleic acid: an oligonucleotide whose sequence corresponds to all or part of an expressed gene or expressed sequence tag (EST). The target nucleic acid may comprise mRNA, cRNA or cDNA.

Target oligonucleotide: a fragment of a target nucleic acid, typically 25 to 100 base pairs long. Target oligonucleotides are circulated over the DNA microarray, defined in detail below, and hybridized with probe oligonucleotides, defined in detail below. Target oligonucleotides are labeled, typically with a fluorescent or radioactive taggant, and can be detected when the target oligonucleotide is hybridized to a probe oligonucleotide.

Probe oligonucleotide: an oligonucleotide bound to a substrate. The sequence of a probe oligonucleotide is chosen so as to hybridize with a specific sequence of a specific target nucleic acid, and will thus hybridize with a target oligonucleotide containing that specific sequence.

Probe spot: a region of a substrate, typically 25 to 200 microns square, onto which a plurality of probe oligonucleotides are bound. At least several billion probe oligonucleotides may be bound at a single probe spot. Preferably, all of these probe oligonucleotides are identical.

DNA microarray: a substrate typically comprising a plurality of probe spots. A single microarray typically comprises from about 1,000 to about 100,000 probe spots. Each probe spot comprises probe oligonucleotides which will hybridize to a specific sequence which is part of a specific target nucleic acid. Multiple probe spots on a microarray may be designed to hybridize to different regions of a common target nucleic acid.

The combined probe spots on a DNA microarray typically hybridize to multiple distinct potential target nucleic acids, e.g., typically greater than 1,000 distinct potential target nucleic acids.

Figure 1:
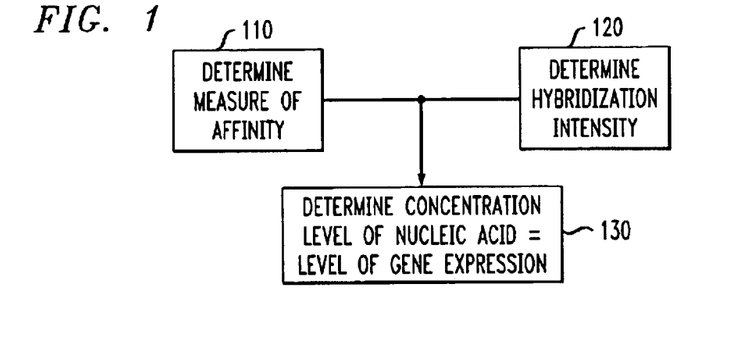
FIG. 1 is a flow chart illustrating an exemplary method for determining gene expression levels according to an embodiment of the present invention.

FIG. 1 is a flow chart showing an exemplary method for determining the concentration level of a target nucleic acid comprising at least one target oligonucleotide. As shown in step 110, a measure of affinity value is determined for the target oligonucleotide and a probe oligonucleotide, the probe oligonucleotide, for example, attached to a DNA microarray. A plurality of measure of affinity values may be determined. The hybridization of a target oligonucleotide and a probe oligonucleotide attached to a microarray is described in detail below, in conjunction with the description of FIG. 2. The measure of affinity value may be determined from rate constants of the hybridization reaction of the target oligonucleotide and the probe oligonucleotide, or from the change in free energy for the hybridization of the target oligonucleotide and the probe oligonucleotide. The measure of affinity for a target oligonucleotide and a probe oligonucleotide is described in more detail below. As shown in step 120, the hybridization intensity value is determined for the target oligonucleotide and the probe oligonucleotide. A plurality of hybridization intensity values may be determined. The determination of the hybridization intensity is described in more detail below. As shown in step 130, the concentration level of the nucleic acid is then determined. The concentration level of the nucleic acid is related to gene expression levels. A plurality of concentration levels of the target nucleic acid may be determined. The determination of the concentration level of the target nucleic acid and the relation between the concentration level of the target nucleic acid and the gene expression level is described in more detail below.

Figure 2:
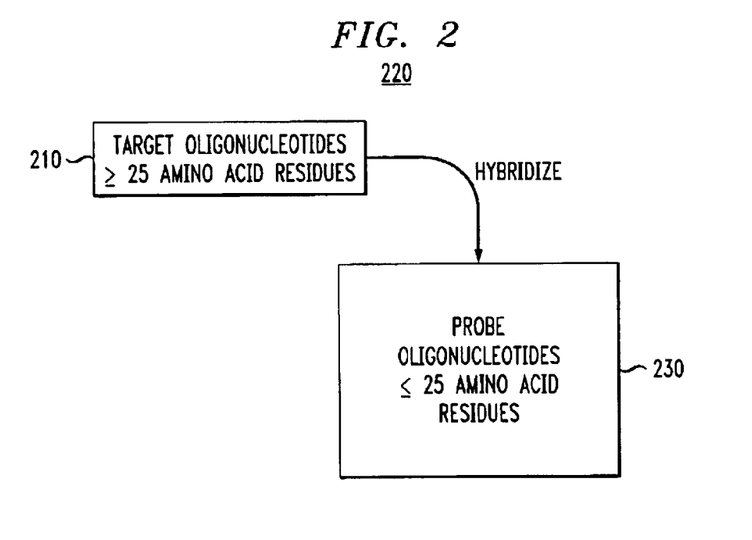
FIG. 2 is a schematic diagram illustrating hybridization on a microarray according to an embodiment of the present invention.

FIG. 2 is a schematic diagram showing an exemplary hybridization of target oligonucleotides 210 and probe oligonucleotides 230 on a DNA microarray 220. Both target oligonucleotides 210 and probe oligonucleotides 230 comprise nucleotide bases. Nucleotide bases include adenine, guanine, cytosine, thymine and uracil.

The teachings of the present invention utilize the physical principles underlying hybridization to produce a simple model of the hybridization process. The model consists of a chemical kinetic representation of the number of hybridized probe oligonucleotides on each probe spot of a microarray, as the number of hybridized probe oligonucleotides is directly proportional to the measured hybridization intensity value for the probe spot.

The individual target oligonucleotides may comprise a greater number of nucleotide bases than the individual probe oligonucleotides. Thus, in an exemplary embodiment, the individual target oligonucleotides comprise greater than or equal to about 25 nucleotide bases, and the individual probe oligonucleotides comprise about 25 nucleotide bases.

The following discussion will focus on the probe oligonucleotides being single-stranded DNA sequences and the target oligonucleotides being mRNA. The mRNA present in a cell is related to the expression levels of a gene encoding the mRNA, as is described in more detail below. However, in accordance with the teachings of the present invention, the target oligonucleotides may be mRNA, cDNA or cRNA.

To form a hybridized microarray, a solution comprising target oligonucleotides 210 is placed in contact with DNA microarray 220. The individual target oligonucleotide sequences of target oligonucleotides 210 hybridize to complementary individual probe oligonucleotides of probe oligonucleotides 230. Microarray 220 is then washed and all non-hybridized target oligonucleotides 210 are removed from microarray 220. All target oligonucleotides 210 that are not hybridized to probe oligonucleotides 230 are thus removed and only those hybridized individual target oligonucleotides of target oligonucleotides 210 remain for analysis.

Figure 3:
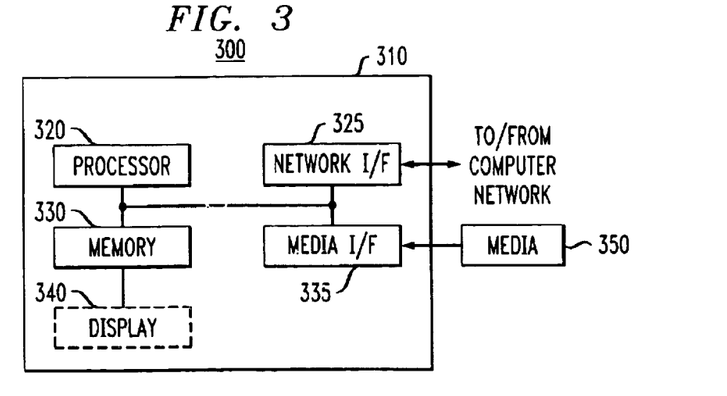
FIG. 3 is a block diagram of an exemplary hardware implementation of a method for determining gene expression levels according to an embodiment of the present invention.

FIG. 3 is a block diagram of a system 300 for determining a concentration level of a target nucleic acid comprising at least one target oligonucleotide in accordance with one embodiment of the present invention. Apparatus 300 comprises a computer system 310 that interacts with a medium 350. Computer system 310 comprises a processor 320, a network interface 325, a memory 330, a media interface 335 and an optional display 340. Network interface 325 allows computer system 310 to connect to a network, while media interface 335 allows computer system 310 to interact with a medium 350, such as a Digital Versatile Disk (DVD) or a hard drive.

As is known in the art, the methods and apparatus discussed herein may be distributed as an article of manufacture that itself comprises a machine readable medium containing one or more programs which when executed implement embodiments of the present invention. For instance, the machine readable medium may contain a program configured to determine a measure of affinity value of the target oligonucleotide with a probe oligonucleotide; determine a hybridization intensity value for the target oligonucleotide and the probe oligonucleotide at a probe spot; and use the measure of affinity value and the hybridization intensity value to determine the concentration level of the target nucleic acid. The machine readable medium may be a recordable medium (e.g., floppy disks, hard drive, optical disks such as a DVD, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used.

Processor 320 can be configured to implement the methods, steps, and functions disclosed herein. The memory 330 could be distributed or local and the processor 320 could be distributed or singular. The memory 330 could be implemented as an electrical, magnetic or optical memory, or any combination of these or other types of storage devices. Moreover, the term "memory" should be construed broadly enough to encompass any information able to be read from or written to an address in the addressable space accessed by processor 320. With this definition, information on a network, accessible through network interface 325, is still within memory 330 because the processor 320 can retrieve the information from the network. It should be noted that each distributed processor that makes up processor 320 generally contains its own addressable memory space. It should also be noted that some or all of computer system 310 can be incorporated into an application-specific or general-use integrated circuit.

Optional video display 340 is any type of video display suitable for interacting with a human user of apparatus 300. Generally, video display 340 is a computer monitor or other similar video display.

The measure of affinity value may comprise a free energy of hybridization of the target oligonucleotide with the probe oligonucleotide. As the free energy of hybridization becomes more negative, the affinity for hybridizing increases. An exemplary method by which the free energy of hybridization may be quantified involves use of the nearest-neighbor (NN) model. The NN model is based on the assumption that the stability of a given nucleotide base pairing is affected by the identity and orientation of neighboring base pairs. For example, as shown in Table 1 below, differences in neighboring bases on one single stranded oligonucleotide impact the stability of the pairing between said oligonucleotide and the single stranded oligonucleotide complementary to it, as represented by the differences in the components of the hybridization free energy, i.e., enthalpy $\Delta H$ and entropy $\Delta S$.

TABLE 1

| Sequence | $\Delta H^0$ (kcal/mol) | $\Delta S^0$ (cal/K · mol) |
|---|---|---|
| AA/TT | −7.9 | −22.2 |
| AT/TA | −7.2 | −20.4 |
| TA/AT | −7.2 | −21.3 |
| CA/GT | −8.5 | −22.7 |
| GT/CA | −8.4 | −22.4 |
| CT/GA | −7.8 | −21.0 |
| GA/CT | −8.2 | −22.2 |
| CG/GC | −10.6 | −27.2 |
| GC/CG | −9.8 | −24.4 |
| GG/CC | −8.0 | −19.9 |
| Init. w/term. G · C | 0.1 | −2.8 |
| Init. w/term. A · T | 2.3 | 4.1 |
| Symmetry correction | 0 | −1.4 |

To account for differences in hybridization enthalpy and entropy for the pairings between oligonucleotides that have a terminal A·T as compared to pairings that have a terminal G·C, the parameters, "initiator with terminal G·C" and "initiator with terminal A·T", are also presented in Table 1. For a more detailed description of the NN model, see J. SantaLucia, Jr., "A Unified View of Polymer, Dumbbell, and Oligonucleotide DNA Nearest-Neighbor Thermodynamics," *Prod. Natl. Acad. Sci.*, 1998, 95, 1460–65, the disclosure of which is incorporated by reference herein.

The change in the free energy of a system upon hybridization may be determined according to the free energy function, $$\Delta G^0 = \Delta H^0 - T\Delta S^0 \quad (1)$$

wherein $\Delta G^0$ represents the change in free energy, $\Delta H^0$ represents the change in enthalpy, T represents the absolute temperature and $\Delta S^0$ represents the change in entropy. Decreasing $\Delta G^0$ implies increasing affinity for hybridization.

The following is an exemplary method for obtaining hybridization intensity values from a DNA microarray to which target oligonucleotides have been hybridized. A plurality of hybridization intensity values may be determined. The plurality of hybridization intensity values may be compared to determine an overall hybridization intensity value, i.e., a mean value.

The hybridization intensity value for the target oligonucleotides and the probe oligonucleotides hybridized on a probe spot of the microarray may be determined experimentally. For example, the target oligonucleotides may be labeled with a fluorescent taggant. When the target oligonucleotides are contacted with the microarray, the target oligonucleotides complementary to probe oligonucleotides on the microarray will be hybridized. In theory, all non-complimentary target oligonucleotides may then be removed. However, cross-hybridization may occur, and thus those target oligonucleotides that have been cross-hybridized will also remain. Cross-hybridization, in this context, refers to target oligonucleotides that are hybridized to probe oligonucleotides, the probe oligonucleotides which were intended to hybridize only to target oligonucleotides resulting from the presence of a different target nucleic acid.

The hybridized target and probe oligonucleotides will be labeled with the fluorescent marker. The fluorescent marker will emit light of a particular wavelength when receiving light of a different wavelength, which may be viewed under a microscope. For example, a confocal microscope scanner may be used to measure the fluorescence of the various probe spots on a DNA microarray. The observed intensity of the fluorescence may be taken as a measure of the hybridization intensity value.

The measure of affinity value and the hybridization intensity value may then be used to determine the concentration level of the target nucleic acid. Determining the concentration level of the target nucleic acid from the measure of affinity value and the hybridization intensity value involves determining a quantitative relationship between the measure of affinity value, the hybridization intensity value and the concentration level of the target nucleic acid.

A quantitative relationship between the measure of affinity value, the hybridization intensity value and the concentration level of the target nucleic acid may be determined from hybridization intensity values measured for a plurality of DNA microarrays which have been hybridized with a plurality of exemplary, known target oligonucleotides at a plurality of known target oligonucleotide concentrations. Such plurality of intensity value measurements has been made publicly available by Affymetrix® (and may be accessed at www.affymetrix.com). Thus, observed hybridization intensity values at known target nucleic acid concentrations may be correlated with particular probe oligonucleotide sequences.

Figure 4:
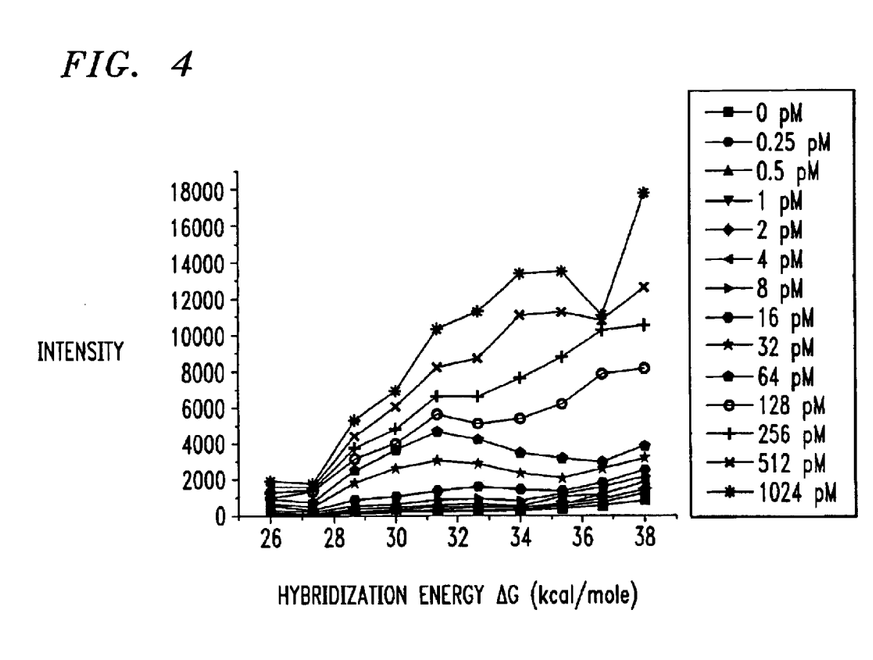
FIG. 4 is a plot showing the dependence of hybridization intensity on hybridization free energy for multiple target oligonucleotide concentrations according to an embodiment of the present invention.

As shown in FIG. 4, these data may be used to show the dependence of hybridization intensity on hybridization free energy over a range of target nucleic acid concentrations. In FIG. 4 the negative value of the hybridization free energy is shown, i.e., as a positive value. Clearly, the hybridization intensity is dependent on the hybridization free energy over the given range of target nucleic acid concentrations, and the hybridization intensity increases with increasingly negative hybridization free energy over the given range of target nucleic acid concentrations.

The hybridization reaction might be represented by the following equation, (2)

wherein the concentration of free, unhybridized probe oligonucleotides on a particular probe spot on the DNA microarray, {free probe}, equals $$\frac{n_P - n_B}{V_{probe}}.$$

The concentration, in a sample solution, of free, unhybridized target oligonucleotides which are complementary to the probe oligonucleotides on the particular probe spot, {free target}, equals $$\frac{n_0 - n_B}{V_{solution}}.$$

The concentration of hybridized probe oligonucleotides and target oligonucleotides on the particular probe spot on the hybridized DNA microarray, {hybridized probe/target}, equals $$\frac{n_B}{V_{probe}}.$$

The variable $n_P$ equals the total number of probe oligonucleotides on the particular probe spot on the DNA microarray. The variable $n_B$ is the total number of bound probe oligonucleotides on the probe spot, as is defined in detail below. The variable $n_0$ equals the total number of target oligonucleotides in the sample solution which are complementary to the particular probe spot. The variable $V_{probe}$ equals the total volume of the probe oligonucleotides on the probe spot. The variable $V_{solution}$ equals the total volume of the sample solution which contains the target oligonucleotides.

The rate constant for the formation of the hybridized probe oligonucleotides and target oligonucleotides on the probe spot is $k_f$. The constant $k_b$ is the rate constant for the uncoupling of the hybridized probe oligonucleotides and target oligonucleotides into free, unhybridized probe oligonucleotides on the probe spot on the DNA microarray and free, unhybridized target oligonucleotides in the sample solution. The constants $k_f$ and $k_b$ may be used to determine a net rate of hybridization, i.e., a net rate of formation of the hybridized probe oligonucleotides and target oligonucleotides on the probe spot.

Like the hybridization free energy, the rate constants $k_f$ and $k_b$ depend upon the nucleotide base sequence of the probe. Thus, the rate constants $k_f$ and $k_b$ will vary from one oligonucleotide probe spot to another, as a consequence of changes in the free energy of hybridization of the probe oligonucleotides on each probe spot to the respective complementary target oligonucleotides. The ratio of $k_f$ to $k_b$ is the equilibrium constant of the hybridization reaction. The larger the ratio of $k_f$ to $k_b$ is, the stronger the tendency for hybridization to occur. Turning to an illustrative example, if a probe oligonucleotide comprises a nucleotide base sequence containing a predominance of adenine (i.e., 5'-AAAAAAAA-3'), the complementary target oligonucleotide comprising a predominance of thymine (i.e., 5'-TTTTTTTT-3'), then the ratio of the rate constants $k_f/k_b$ would be less than the instance wherein the probe oligonucleotide comprises a nucleotide base sequence containing a predominance of guanine (i.e., 5'-GGGGGGGG-3'), the complementary target oligonucleotide comprising a predominance of cytosine (i.e., 5'-CCCCCCCC-3').

The teachings of the present invention may be used to predict the concentration of the complementary target oligonucleotides. From equation 2 above, the following rate equation has been deduced, $$\frac{\partial n_B}{\partial t} = k_f(n_P - n_B)\left(\frac{n_0 - n_B}{V_{solution}}\right) - k_b n_B. \quad (3)$$

wherein, assuming equilibrium, i.e., $$\frac{\partial n_B}{\partial t} = 0,$$

and assuming $n_B \ll n_0$, $$n_B = \frac{n_P c}{c + n_e} \quad (4)$$

and wherein $$n_e = \frac{k_b}{k_f},$$

and $$c = \frac{n_0}{V_{solution}}$$

is the target oligonucleotide concentration. A model may be constructed wherein $n_e$ is assumed to be dependent on the free energy of hybridization (and therefore will vary depending on the hybridization free energy of a particular probe oligonucleotide) and $n_p$ is assumed to be independent of the free energy of hybridization.

The measured hybridization intensity value is directly related to $n_B$. Assuming linear proportionality, Intensity equals $fn_B$, wherein f is a constant. The following equation may then be used to correlate the hybridization free energy, the hybridization intensity and the target oligonucleotide concentration, $$\text{Intensity} = \frac{n_p' c}{c + n_e} + bg \quad (5)$$

wherein the variable c equals the target oligonucleotide concentration expressed in moles, and $n_p' = fn_p$ is the saturation intensity of the fluorescence. The variable bg is an energy dependent background term which may be determined by setting the target oligonucleotide concentration, c, to a value of zero. However, to give data from lower concentrations comparable weight to that from higher concentrations, the log of the intensity value may be taken. Thus, in an exemplary embodiment, the log of equation 5 is used, $$\log(\text{Intensity}) = \log\left(\frac{n_p' c}{c + n_e} + bg\right) \quad (6)$$

Application of equation 6 to a plurality of experimental measurements for which both the hybridization intensity values of the probe spots and the actual concentrations of the target nucleic acids are known, allows the determination of expressions for $n_e$ and bg as functions of free energy of hybridization, as well as the value of the assumed constant $n_p'$.

Figure 5:
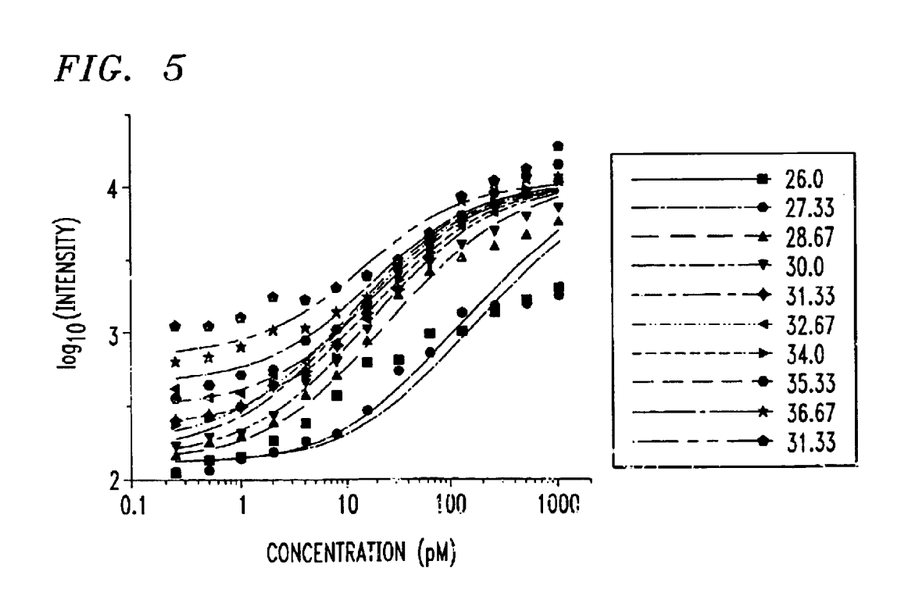
FIG. 5 is a plot showing hybridization intensity as a function of target oligonucleotide concentration for several hybridization free energy bins according to an embodiment of the present invention.

Thus, known hybridization intensity values as a function of known and binned hybridization free energy values, measured at various known target nucleic acid concentrations, for multiple target nucleic acids, such as the data shown plotted in FIG. 5, may be used to define the parameters of the above equation, including the values of $n_e$ and bg as function of hybridization free energy, as well as the constant $n_P$. Once the parameters for the functional dependence of $n_e$ and bg on the free energy of hybridization are defined for a given set of target nucleic acids, any hybridization intensity values and hybridization free energy values may be used to determine the corresponding $n_e$ and bg values. Subsequently, equation 6 can be used to determine target oligonucleotide concentrations.

Specifically, data such as that shown plotted in FIG. 5, are fit to equation 6, and may be used to determine empirical functions which describe the dependence of $n_e$ and bg as a function of hybridization free energy, as described in detail below. A constant value for $n_p'$ is also obtained through this fitting procedure. In FIG. 5 the solid lines show best fit values of the data fit to equation 6 in the manner described above. Each curve shown represents binned data corresponding to a particular narrow range (1.333 kcal/mole in FIG. 5) of hybridization free energy values. As such, each discrete hybridization free energy range, or bin has a particular $n_e$ and bg value.

Figure 6:
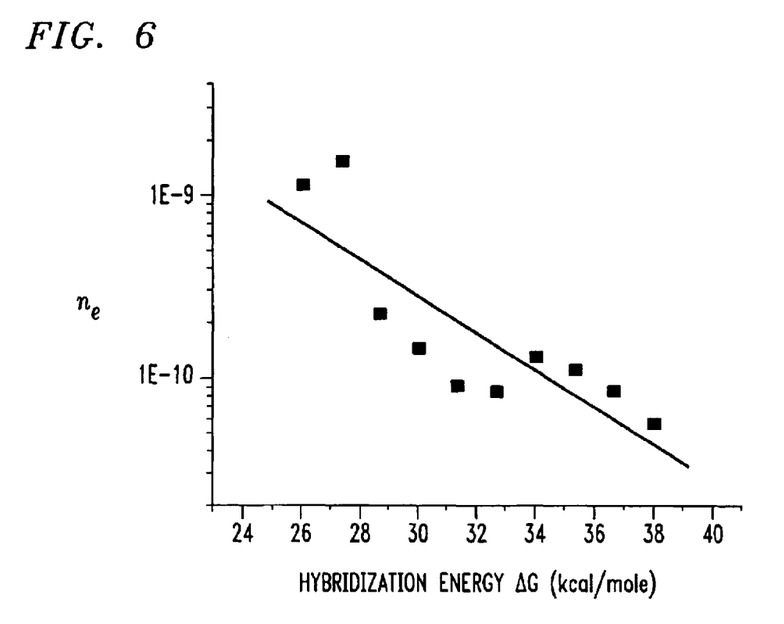
FIG. 6 is a plot showing the variable $n_e$ as a function of hybridization free energy according to an embodiment of the present invention.
Figure 7:
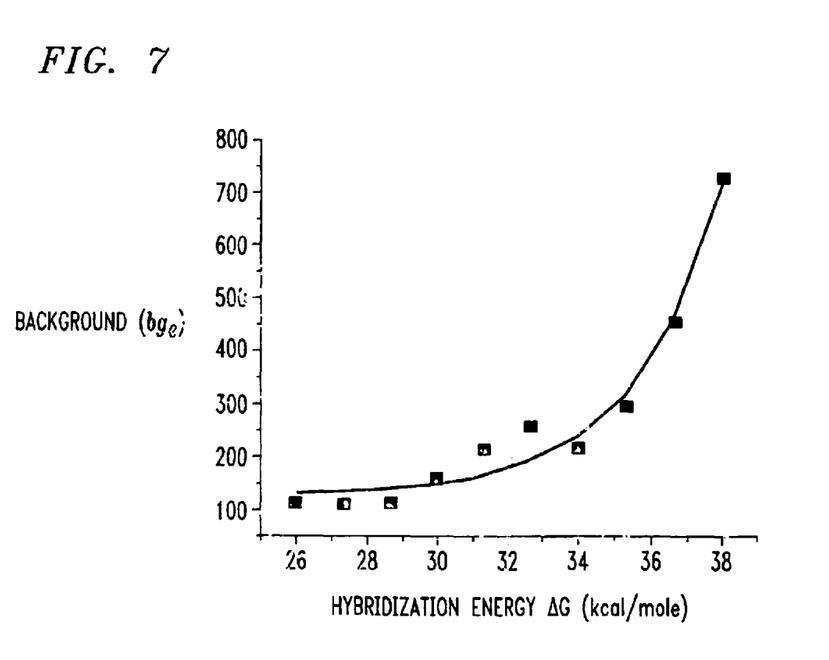
FIG. 7 is a plot showing the variable bg as a function of hybridization free energy according to an embodiment of the present invention.

Once the values of $n_e$ and bg have been determined for each hybridization free energy bin, the values of $n_e$ and bg are correlated with the hybridization free energy, as is shown in FIG. 6 and FIG. 7, respectively. FIG. 6 is a plot showing $n_e$ as a function of the negative of the hybridization free energy. The values of $n_e$ decrease as the value of each hybridization free energy bin decreases. FIG. 7 is a plot showing bg as a function of the negative of the hybridization free energy. The values of bg increase as the values of each of the hybridization free energy bins decreases. From the correlation of $n_e$ and bg with hybridization free energy, for each hybridization free energy bin, a functional equation may be determined. For example, from the data shown in FIG. 6 and FIG. 7, the functional equation for $n_e$ equals $3.1 \times 10^5 \exp(-0.235 \Delta G)$ and the functional equation for bg equals $127 + 6 \times 10^{-5} \exp(0.423 \Delta G)$, wherein $\Delta G$ represents the negative of the value of the hybridization free energy. The value of $n_p'$ obtained from the above fitting procedure is 9494.

Using the above expressions for $n_e$ and bg as functions of the free energy of hybridization, equation 6 may be used with the experimentally determined hybridization intensity values from the probe spots for a particular target oligonucleotide, and the hybridization free energy values of those probe spots, to determine the target oligonucleotide concentration. When data is collected from multiple probe oligonucleotides corresponding to a single target nucleic acid, an overall value for the concentration of that nucleic acid is determined. In one embodiment of the present invention, determining the concentration level of the target nucleic acid from multiple probe oligonucleotides may be accomplished by averaging the values obtained from equation 6 for each of the probe spots which hybridize with a region of the target nucleic acid under consideration.

Figure 8:
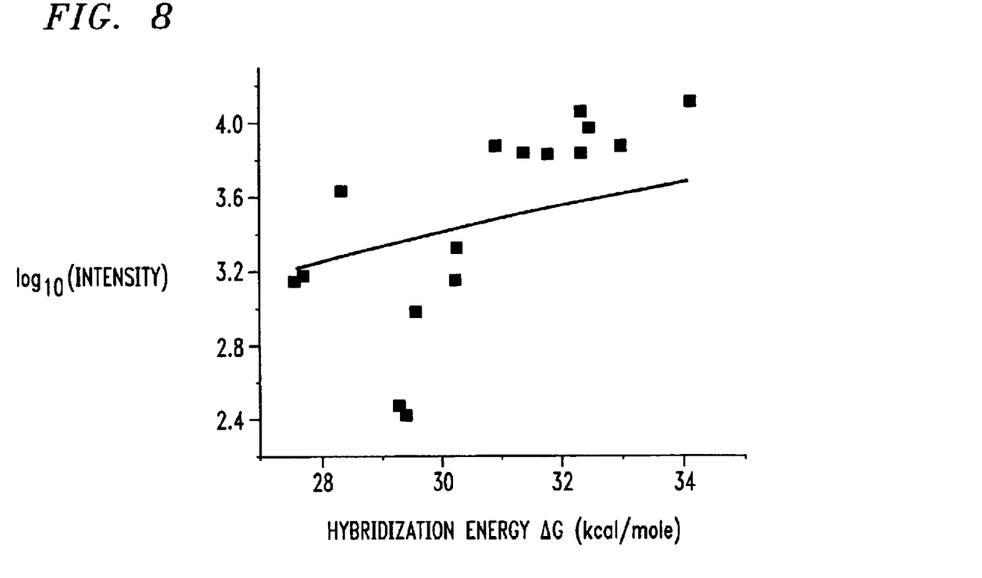
FIG. 8 is a plot showing target oligonucleotide concentrations determined from hybridization intensity and hybridization free energy according to an embodiment of the present invention.

In another exemplary embodiment of the present invention, the hybridization intensity values of all of the probe spots which hybridize to regions of a particular target nucleic acid may be fit to equation 6 simultaneously. An exemplary use of equation 6 to determine the target oligonucleotide concentration for a given sample is shown in FIG. 8. FIG. 8 shows the hybridization intensity values of the probe spots hybridized to regions of the target nucleic acid that encodes the protein phosphodiesterase 1A. The values are plotted as a function of the free energy of hybridization of the individual probe spots. Fitting the data in FIG. 8 to equation 6, the target oligonucleotide concentration may be calculated. Sixteen probe spots were used in this particular case. A best fit line for all the probe spot hybridization intensity values is shown as a solid line in FIG. 8.

In an exemplary embodiment, a method for predicting the target nucleic acid concentration is provided. In the exemplary method, the measure of affinity value of the target oligonucleotide with the probe oligonucleotide is determined. An observed hybridization intensity is then obtained and an expected hybridization intensity value is determined. The observed hybridization intensity value, the expected hybridization intensity value and the measure of affinity value are compared for a plurality of probe spots corresponding to the target nucleic acid, to determine a unique predicted concentration of that nucleic acid.

In another exemplary embodiment, the present method involves a plurality of probe oligonucleotides. Further, an observed hybridization intensity value for the probe oligonucleotide is obtained, and the observed hybridization intensity value is used to determine a concentration level of the target nucleic acid value for a plurality of probe oligonucleotides, to obtain a plurality of concentration levels of the target nucleic acid. The plurality of concentration levels of the target nucleic acid are compared to determine an overall concentration level of the target nucleic acid.

As FIG. 8 illustrates, outlying data points that will affect the analysis may occur. Accordingly, as described above, cross-hybridization may occur. Additionally, statistical fluctuations may occur that result in statistically outlying data points that will affect the analysis. To accommodate for the variations, all data points that show a predetermined deviation from the hybridization intensity value predicted by the best fit of equation 6 to the data are discarded, and the remaining hybridization intensity values are then refitted to equation 6. Thus, the statistically outlying hybridization intensity values are removed and the target nucleic acid concentration is then determined again using the remaining hybridization intensity values. In an exemplary embodiment, all points that are greater than or equal to one standard deviation beyond the average deviation of data points from the best fit value, may be removed. Thus, all points that are greater than or equal to one standard deviation beyond the average deviation of the hybridization intensity values predicted using the best fit value of the target nucleic acid concentration are discarded, and the remaining target oligonucleotide values are analyzed. As such, the 16 hybridization intensity values of the probe spots which hybridize to the target nucleic acid may be used to determine the target oligonucleotide concentration.

The target oligonucleotide concentration is an efficient and accurate way to approximate gene expression levels. In a cell, genes are typically expressed by the transcription of the gene material, i.e., DNA into mRNA which is then translated into proteins. By sampling the cell contents and identifying and quantifying the mRNA levels present, researchers can determine which genes, i.e., which DNA, are being expressed by the cell. The use of microarrays allows researchers to study a wide variety of genes at the same time, permitting comparative gene expression studies.

Additionally, variations may occur within a single probe spot. Particularly, while each probe oligonucleotide on a probe spot is purported to comprise the same number of nucleotide bases, many do not. On an Affymetrix® DNA microarray for which each probe spot is ideally comprised of probe oligonucleotides all being 25 nucleotide bases long, in fact only about eight percent of the probe oligonucleotides are actually 25 nucleotide bases in length. For a detailed description of microarrays, see J. E. Forman, et al., "Thermodynamics of Duplex Formation and Mismatch Discrimination on Photolithographically Synthesized Oligonucleotide Arrays," *Molecular Modeling of Nucleic Acids, ACS Symposium Series*, v. 692, p. 206 (1998), the disclosure of which is incorporated by reference herein. Thus, there may be a distribution of probe oligonucleotide lengths within a given probe spot on a DNA microarray. In the instance where there is a distribution of probe oligonucleotides of varying lengths, the target oligonucleotide concentration may be determined according to the equation, $$\text{Intensity} = \sum_{i=1}^{25} prob(i)\left\{\frac{n_P c}{c + n_e(i)} + bg(i)\right\} \quad (7)$$

wherein for each variable probe oligonucleotide length, i, the term $n_e(i)$ may be determined from data from probe spots for which both the hybridization intensity and the actual target nucleic acid concentration are known. In another embodiment, the value of $n_e$ may be taken to be the value predicted from equilibrium statistical mechanics, $$n_e = e^{-\Delta G/k_B T} \quad (8)$$

The variable i equals the number of nucleotide bases in the probe oligonucleotide. Thus, the value prob(i) equals the probability that a probe oligonucleotide within a given probe spot has a particular number of nucleotide bases, i.e., a length, of from one nucleotide base to a total of 25 nucleotide bases.

Although illustrative embodiments of the present invention have been described herein, it is to be understood that the invention is not limited to those precise embodiments, and that various other changes and modifications may be effected therein by one skilled in the art without departing from the scope or spirit of the invention. The following example is provided to illustrate the scope and spirit of the present invention. Because this example is given for illustrative purposes only, the invention embodied therein should not be limited thereto.

EXAMPLE

Figure 9:
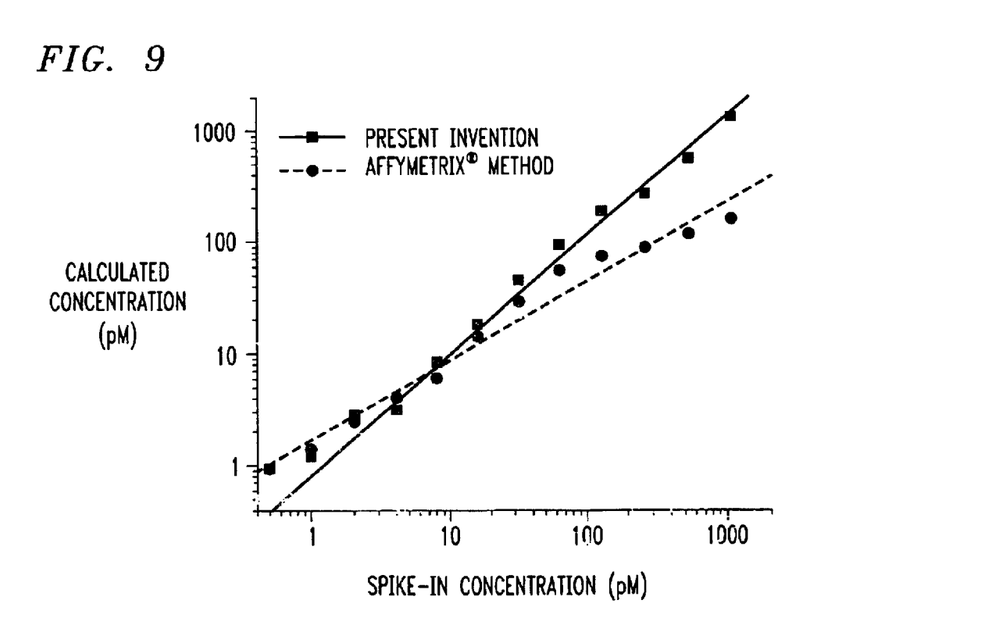
FIG. 9 is a plot showing target oligonucleotide concentrations determined by the teachings of the present invention and by the Affymetrix® method, as compared to known target oligonucleotide concentrations according to an embodiment of the present invention.

Publicly available data from Affymetrix® (www.affymetrix.com) was used to test the method of the present invention. The data included about 840 measurements of target nucleic acids with known concentrations. Specifically, at each known concentration there were about 60 data sets representing two to 12 replicates of each of 14 target nucleic acids, each encoding a specific gene. The results are shown in FIG. 9. FIG. 9 is a plot showing target oligonucleotide concentrations determined by the present invention and by the Affymetrix® method, as compared to known target oligonucleotide concentrations. Specifically, FIG. 9 shows the median target nucleic acid concentration values determined at each known target nucleic acid concentration using the publicly available data, according to the present method and also according to the Affymetrix® Microarray Suite V. 5 analysis. The results are plotted as a function of the known target nucleic acid concentration values. A perfect linearity between the determined target nucleic acid concentrations and the known target nucleic acid concentrations would produce a slope of unity in a plot wherein both the known and determined target nucleic acid concentrations are plotted on logarithmic scales.

According to the Affymetrix® method, gene expression levels are determined by grouping individual probe spots in pairs. Each pair of probe spots comprises one individual oligonucleotide probe sequence that is exactly complementary to a given individual target oligonucleotide sequence, called a perfect match oligonucleotide sequence (hereinafter "perfect match sequence"). Each pair of oligonucleotide probe sequences also comprises one individual probe oligonucleotide sequence that has exactly one nucleotide base that is not complementary to the corresponding nucleotide base in the given individual target oligonucleotide sequence, called a mismatched oligonucleotide sequence (hereinafter "mismatched sequence"). Thus, the mismatched sequence has the same nucleotide base sequence as the perfect match sequence, except for the one mismatched nucleotide base. The difference between the degree of hybridization of the target oligonucleotide sequence to the perfect match sequence and the degree of hybridization of the target oligonucleotide sequence to the mismatched sequence may be used to determine the expression level of the corresponding gene. While the present invention described herein does not utilize mismatched sequence probe spot hybridization intensity for analysis, it is to be understood to one skilled in the art that the difference between the perfect match sequence probe spot hybridization intensity and the corresponding mismatched sequence probe spot hybridization intensity may be incorporated into the present invention as the observed hybridization intensity measurement for each probe oligonucleotide sequence.

As is shown in FIG. 9, the slope for the calculated target nucleic acid concentrations plotted against the known target nucleic acid concentration on logarithmic scales determined using the present invention equals 1.08. The slope for the calculated target nucleic acid concentrations plotted against the known target nucleic acid concentrations on logarithmic scales determined using the Affymetrix® analysis equals 0.71. Thus, with regard to a linear response of calculated target nucleic acid concentration as a function of known nucleic acid concentration, use of the present invention yields more accurate calculated values.

What is claimed is:

1. A method for determining a concentration level of a target nucleic acid, the target nucleic acid comprising at least one target oligonucleotide, the method comprising the steps of:
   determining a measure of affinity value of the target oligonucleotide with a probe oligonucleotide;
   determining a hybridization intensity value for the target oligonucleotide and the probe oligonucleotide at a probe spot; and
   using the measure of affinity value and the hybridization intensity value to determine the concentration level of the target nucleic acid.

2. The method of claim 1, wherein the measure of affinity value comprises a free energy of hybridization of the target oligonucleotide with the probe oligonucleotide.

3. The method of claim 1, wherein the measure of affinity value comprises a net rate of hybridization of the target oligonucleotide with the probe oligonucleotide.

4. The method of claim 1, wherein the method is carried out for a plurality of probe spots.

5. The method of claim 4, wherein the plurality of probe spots are attached to a microarray.

6. The method of claim 1, wherein the hybridization intensity value is determined using fluorescence.

7. The method of claim 1, comprising a plurality of measure of affinity values, hybridization intensity values and concentration levels of the target nucleic acid.

8. The method of claim 7, further comprising the step of comparing the plurality of hybridization intensity values to determine an overall hybridization intensity value.

9. The method of claim 1, comprising a plurality of probe oligonucleotides.

10. The method of claim 9, further comprising the steps of:
    obtaining an observed hybridization intensity value for the probe oligonucleotide at the probe spot;
    using the observed hybridization intensity value to determine a concentration level of the target nucleic acid;
    performing the steps of obtaining and using for the plurality of probe oligonucleotides to obtain a plurality of concentration levels of the target nucleic acid; and
    comparing the plurality of concentration levels of the target nucleic acid to determine an overall concentration level of the target nucleic acid.

11. The method of claim 10, wherein the using step further comprises the step of removing probe spots with statistically outlying observed hybridization intensity values.

12. The method of claim 1, wherein the step of determining the measure of affinity value of the target oligonucleotide with a probe oligonucleotide further comprises the step of correlating observed hybridization intensity values at known target nucleic acid concentrations with probe oligonucleotide sequences.

13. The method of claim 1, wherein the measure of affinity value is calculated on the basis of the physical principles of hybridization.

14. A method for predicting a concentration level of a target nucleic acid, the target nucleic acid comprising at least one target oligonucleotide, the method comprising the steps of:
    determining a measure of affinity value of the target oligonucleotide with a probe oligonucleotide at a probe spot;
    obtaining an observed hybridization intensity value;
    determining an expected hybridization intensity value; and
    comparing the measure of affinity value, the observed hybridization intensity value and the expected hybridization intensity value for a plurality of probe spots to determine a unique predicted target nucleic acid concentration.

15. The method of claim 14, wherein the obtaining step further comprises the step of removing probe spots from the plurality of probe spots having statistically outlying observed hybridization intensity values.

16. An apparatus for determining a concentration level of a target nucleic acid, the target nucleic acid comprising at least one target oligonucleotide, the apparatus comprising:
    a memory; and
    at least one processor, coupled to the memory, operative to:
    determine a measure of affinity value of the target oligonucleotide with a probe oligonucleotide;
    determine a hybridization intensity value for the target oligonucleotide and the probe oligonucleotide at a probe spot; and
    use the measure of affinity value and the hybridization intensity value to determine the concentration level of the target nucleic acid.

17. An article of manufacture for determining a concentration level of a target nucleic acid, the target nucleic acid comprising at least one target oligonucleotide, comprising a machine readable medium containing one or more programs which when executed implement the steps of:
    determining a measure of affinity value of the target oligonucleotide with a probe oligonucleotide;
    determining a hybridization intensity value for the target oligonucleotide and the probe oligonucleotide at a probe spot; and
    using the measure of affinity value and the hybridization intensity value to determine the concentration level of the target nucleic acid.

* * * * *